United States Patent
Qian et al.

(10) Patent No.: US 10,632,163 B2
(45) Date of Patent: Apr. 28, 2020

(54) **FRESH *OPHIOCORDYCEPS SINENSIS* PRODUCT AND PREPARATION METHOD THEREOF**

(71) Applicants: SUNSHINE LAKE PHARMA CO., LTD., Dongguan, Guangdong (CN); Yichang Shanchengshuidu Cordyceps Co., LTD., Yidu, Yichang, Hubei (CN)

(72) Inventors: Zhengming Qian, Dongguan (CN); Zhong Ai, Dongguan (CN); Wenjia Li, Dongguan (CN); Guangrong Li, Dongguan (CN); Wenxiang Zhang, Dongguan (CN); Xiangqin Xu, Guangdong (CN); Xinfa Tang, Guangdong (CN)

(73) Assignee: NORTH & SOUTH BROTHER PHARMACY INVESTMENT COMPANY LIMITED, Wanchai (HK)

( * ) Notice: Subject to any disclaimer, the term of this patent is extended or adjusted under 35 U.S.C. 154(b) by 22 days.

(21) Appl. No.: 15/857,637

(22) Filed: Dec. 29, 2017

(65) Prior Publication Data
US 2018/0185424 A1 Jul. 5, 2018

(30) Foreign Application Priority Data
Jan. 5, 2017 (CN) .......................... 2017 1 0006514

(51) Int. Cl.
*A61K 36/068* (2006.01)

(52) U.S. Cl.
CPC ........ *A61K 36/068* (2013.01); *A61K 2236/13* (2013.01)

(58) Field of Classification Search
CPC .......................... A61K 2236/13; A61K 36/068
See application file for complete search history.

(56) References Cited

U.S. PATENT DOCUMENTS

2016/0345504 A1* 12/2016 Yang ...................... A01G 18/00
2017/0067011 A1*  3/2017 Cao .......................... C12N 1/14

FOREIGN PATENT DOCUMENTS

| CN | 101317562 | 12/2008 |
|----|-----------|---------|
| CN | 102178226 |  9/2011 |
| CN | 102406164 |  4/2012 |
| CN | 103740592 |  4/2014 |
| CN | 104890931 |  9/2015 |
| CN | 105199956 | 12/2015 |
| CN | 106265770 |  1/2017 |

OTHER PUBLICATIONS

CN 103706582.*
CN 103706582translation.*
Eng. translation of the abstract of CN 101317562A.
Eng. translation of the abstract of CN 102178226B.
Eng. translation of the abstract of CN 102406164A.
Eng. translation of the abstract of CN103740592B.
Eng. translation of the abstract of CN 104890931A.
Eng. translation of the abstract of CN 105199956A.
Eng. translation of the abstract of CN 106265770A.

* cited by examiner

*Primary Examiner* — Erik Kashnikow
*Assistant Examiner* — Preston Smith
(74) *Attorney, Agent, or Firm* — Kam Wah Law

(57) ABSTRACT

The present disclosure pertains to the field of processing fresh traditional Chinese medicinal materials, and particularly relates to a method of preparing a fresh *Ophiocordyceps sinensis* product. The fresh *Ophiocordyceps sinensis* product may be prepared by the following steps: 1) stripping off mud from a fresh *Ophiocordyceps sinensis*; 2) brushing with flowing water; 3) cleaning ultrasonically; 4) humidifying the cleaned fresh *Ophiocordyceps sinensis* with atomized water for 15 to 20 minutes; 5) packaging the humidified fresh *Ophiocordyceps sinensis* by sealing it in a tube charged with a modified-atmosphere; and 6) storing the tube at a low temperature; wherein step 1) to step 4) are carried out at a temperature from 3 to 15° C. The present disclosure also relates to a fresh *Ophiocordyceps sinensis* product prepared by the above method.

12 Claims, No Drawings

FRESH *OPHIOCORDYCEPS SINENSIS* PRODUCT AND PREPARATION METHOD THEREOF

CROSS-REFERENCE TO RELATED APPLICATION

This application claims priority to Chinese Patent Application No. 201710006514.1, filed on Jan. 5, 2017, which is hereby incorporated by reference in its entirety.

FIELD

The present invention pertains to the field of processing fresh traditional Chinese medicinal materials, and relates generally to a fresh *Ophiocordyceps sinensis* product and a preparation method thereof, which can achieve the purpose of preserving the *Ophiocordyceps sinensis* fresh and safe for consumption.

BACKGROUND OF THE INVENTION

*Ophiocordyceps sinensis* is a kind of advanced nourishing precious traditional Chinese medicinal material, which contains a variety of nutrients and active ingredients comprising nucleosides, polysaccharides, sterols, fatty acids, proteins, polypeptides and volatile components, etc. It has the functions of anti-tumor, regulating immune system, promoting cellular repair, anti-free radicals, anti-oxidation, anti-aging, protecting myocardial and vascular cells, improving cardiovascular function, protecting liver, protecting kidneys, regulating respiratory system, regulating blood system and regulating blood lipids, etc.

Most *Ophiocordyceps sinensis* currently on the market are dried *Ophiocordyceps sinensis*; a large number of volatile components will evaporate in a process of drying *Ophiocordyceps sinensis*, part of the nutrition will be lost, active ingredients will be inactivated, and taking a substantial decline in taste. However, fresh *Ophiocordyceps sinensis* can maximize the retention of their nutrients and active ingredients, while maintaining its unique fragrance and crisp mouthfeel. The preservation of fresh *Ophiocordyceps sinensis* is an important problem at present, and the pre-cleaning procedures will affect the quality of preservation to a certain extent. A large number of parasites, heavy metals, pathogenic mildew and bacteria exist on the surface of freshly harvested fresh *Ophiocordyceps sinensis*, which cannot be completely cleaned by conventional methods, and therefore cannot be consumed directly. The cleaning method provides a basis for subsequent preservation. Methods regarding the processing and preservation of fresh *Ophiocordyceps sinensis* were disclosed, such as:

Chinese patent application (CN 102406164A) disclosed a method of processing fresh *Ophiocordyceps sinensis* and a method for preparing canned *Ophiocordyceps sinensis*, which mainly comprises storing cleaned fresh *Ophiocordyceps sinensis* at an ultra-low temperature of −70° C.; thawing and grading the fresh *Ophiocordyceps sinensis*; soaking the fresh *Ophiocordyceps sinensis* in tap water based preservation solution containing citric acid and sodium erythorbate; testing and sterilizing at a high temperature; and preparing canned *Ophiocordyceps sinensis*.

Chinese patent for invention (CN 103740592B) disclosed a method of preserving the freshness of *Ophiocordyceps sinensis*, which disclosed that after washing the head, stroma and body of *Ophiocordyceps sinensis* respectively, the washed fresh *Ophiocordyceps sinensis* were soaked into an acidic 0.9% sodium chloride solution for 5-8 minutes in order to prevent loss of nutrients and active substances; and then the fresh *Ophiocordyceps sinensis* were cooled rapidly at −75° C. for 5-12 hours, and placed in a vacuum-freezer at −5--25° C. for storage.

Chinese patent for invention (CN 102178226B) disclosed a method of processing fresh *Ophiocordyceps sinensis*, which mainly comprises refrigerating fresh *Ophiocordyceps sinensis* at a low temperature below −65° C.; setting up a method for cleaning and sterilizing using a combination of ultrasonic waves and ozone; and finally storing the fresh *Ophiocordyceps sinensis* at 0° C.

Chinese patent application (CN105199956A) disclosed a method of preserving the freshness of *Ophiocordyceps sinensis*, which mainly comprises washing *Ophiocordyceps sinensis* with a certain concentration of alcoholic solution; spraying honey water to cover the surface of the *Ophiocordyceps sinensis* to retain nutrition and moisture; conducting air drying and dehumidification, and quick-freezing at −30° C. and storing in a cold storage warehouse under −5° C.

Some of the above prior art preservation ideas include direct freezing at ultra-low temperature (−70° C.), some were quick-freezing (−30° C. to −75° C.) for locking active ingredients and storage at a low temperature (under 0° C.), and others, in order to retain nutrients and moisture or color, include the steps of soaking in acidic water or spraying honey water; these fresh *Ophiocordyceps sinensis* provided in the above prior art retained most nutrients and active ingredients compared with dry *Ophiocordyceps sinensis* products. However, when thawed for consumption, its freshness decreased significantly, even cell viability was lost. In addition, the *Ophiocordyceps sinensis* are softened and moistened, causing the appearance, mouthfeel and nutrition of these fresh *Ophiocordyceps sinensis* to be seriously affected. Meanwhile, soaking in acidic water and spraying with honey water would affect the original savory taste of fresh *Ophiocordyceps sinensis*.

In order to retain the original nutrients and active ingredients, as well as freshness and mouthfeel after thawing for consumption, a fresh *Ophiocordyceps sinensis* product and a preparation method thereof are needed to maintain the appearance, color, nutritional value and mouthfeel, and to be able to be stored for a long time, thereby the preservation of freshness can really be achieved.

SUMMARY OF THE INVENTION

Through a large number of experiments, the inventors of the present invention found that the best way to retain the savory taste and mouthfeel of fresh *Ophiocordyceps sinensis* is to maintain the vitality of the *Ophiocordyceps sinensis* cells. However, under the conventional conditions of maintaining cell vitality, the storage period cannot be long and nutrients will gradually be lost. In order to retain nutrients for a longer time, it can be stored at an ultra-low temperature freezing environment below −25° C. or quick freezing below −25° C. and then stored at a low temperature. These methods can store fresh *Ophiocordyceps sinensis* for a longer time and maintain its quality, but cannot guarantee the freshness of the fresh *Ophiocordyceps sinensis*. In addition, the fresh *Ophiocordyceps sinensis* having active cells may be affected by frostbite easily, and the cells may be frozen to death. Softening and moistening could happen after thawing, which could affect appearance, savory flavor, mouthfeel and micronutrients of the fresh *Ophiocordyceps*

*sinensis*; therefore the preservation effect is inversely proportional to the preservation time.

In order to find a method for retaining the savory flavor, mouthfeel, nutraceutical and active ingredients of fresh *Ophiocordyceps sinensis* and storing for a long time, the present disclosure provided a set of scientific and rational manufacturing process of fresh *Ophiocordyceps sinensis* through multi-dimensional study combining with taking multiple factors into consideration, comprises stripping off mud, washing at a low temperature over the whole process, packaging fresh *Ophiocordyceps sinensis* individually with modified atmosphere having a certain humidity. The process is simple and easy to control, maximal unique flavor and nutrients of fresh *Ophiocordyceps sinensis* can be retained, and also a good appearance and color can be retained, the preserved condition also last long.

The purpose of the present disclosure is achieved by the following technical scheme:

In one aspect, the present disclosure provides a method of preparing a fresh *Ophiocordyceps sinensis* product comprising the following steps:

1) stripping off mud covered on one or more fresh *Ophiocordyceps sinensis* at a temperature from about 3° C. to about 15° C.;

2) brushing the one or more fresh *Ophiocordyceps sinensis* with flowing water at a temperature from about 3° C. to about 15° C.;

3) cleaning ultrasonically the one or more fresh *Ophiocordyceps sinensis* with water at a temperature from about 3° C. to about 15° C.;

4) humidifying the cleaned one or more fresh *Ophiocordyceps sinensis* with atomized water at a temperature from about 3° C. to about 15° C. for about 10 minutes to about 40 minutes;

5) packaging the humidified one or more fresh *Ophiocordyceps sinensis* by sealing the one or more humidified fresh *Ophiocordyceps sinensis* in a tube charged with a modifying atmosphere comprising oxygen from about 3% to about 7%; nitrogen from about 75% to about 92%; and carbon dioxide from about 5% to about 18% at a temperature from about 3° C. to about 15° C.; and 6) storing the tube at a low temperature.

In some embodiments, the stripping step 1) is performed at about 5° C. to about 10° C.; the brushing step 2) is performed at about 3° C. to about 6° C.; the cleaning step 3) is performed at about 3° C. to about 6° C.; step 4) is performed at about 5° C. to about 10° C.; step 5) is performed at about 5° C. to about 10° C.

In some embodiments, the stripping step 1) is performed at about 5° C. to about 10° C.

In some embodiments, the brushing step 2) is performed at about 3° C. to about 6° C.; preferably, at about 4° C.

In some embodiments, the cleaning step 3) is performed at about 3° C. to about 6° C.; preferably, at about 4° C.

In some embodiments, step 4) is performed at about 5° C. to about 10° C.

In some embodiments, step 5) is performed at about 5° C. to about 10° C.

In some embodiments, the humidifying step 4) is carried out for about 15 minutes to about 20 minutes.

In some embodiments, the humidifying step 4) is carried out in an ultrasonic humidifier.

In some embodiments, both the flowing water used in the brushing step 2) and the water used in the cleaning step 3) are germfree physiological saline.

In some embodiments, the cleaning step 3) is performed within 1 hour after the brushing step.

In some embodiments, the modified-atmosphere in step 5) comprises about 5% of oxygen, about 85% of nitrogen and about 10% of carbon dioxide by volume fraction, based on the total amount of oxygen, nitrogen and carbon dioxide.

In some embodiments, humidity in the tube in the packaging step 5) is controlled in a range from about 65% to about 75%.

In some embodiments, the stripping step 1) refers to stripping off mud covered on the one or more fresh *Ophiocordyceps sinensis* at a temperature from about 5° C. to about 10° C.

In some embodiments, the brushing step 2) refers to brushing the one or more fresh *Ophiocordyceps sinensis* by using a soft brush with flowing germfree physiological saline precooled to a temperature from about 3° C. to about 6° C. for about 1 minute to about 2 minutes after the stripping step; preferably, the flowing germfree physiological saline is pre-cooled to about 4° C.

In some embodiments, the cleaning step 3) refers to cleaning ultrasonically the one or more fresh *Ophiocordyceps sinensis* in germfree physiological saline pre-cooled to a temperature from about 3° C. to 6° C. for about 1 minute to about 2 minutes within 1 hour after the brushing step; and wherein the ultrasonic power is from about 300 W to about 500 W; preferably, the germfree physiological saline is pre-cooled to about 4° C.

In some embodiments, the stripping step 1) refers to stripping off mud covered on the one or more fresh *Ophiocordyceps sinensis* at a temperature from about 5° C. to about 10° C.; the brushing step 2) refers to brushing the one or more fresh *Ophiocordyceps sinensis* by using a soft brush with flowing germfree physiological saline precooled to a temperature from about 3° C. to about 6° C. for about 1 minute to about 2 minutes after the stripping step; the cleaning step 3) refers to cleaning ultrasonically the one or more fresh *Ophiocordyceps sinensis* in germfree physiological saline precooled to a temperature from about 3° C. to 6° C. for about 1 minute to about 2 minutes within 1 hour after the brushing step; and wherein the ultrasonic power is from about 300 W to about 500 W.

In some embodiments, the cleaning step 3) further comprises cleaning ultrasonically a second time for about 0.5 minutes to about 1 minute with another germfree physiological saline precooled to a temperature from about 3° C. to 6° C., the ultrasonic power is from about 300 W to about 500 W; preferably, the germfree physiological saline is pre-cooled to about 4° C.

In some embodiments, the stripping off mud refers to removing mud, eggs, and *Phytophthora infestans* from surface and wrinkles of the one or more fresh *Ophiocordyceps sinensis* by using a soft wool brush.

In some embodiments, the low temperature in step 6) is from about −8° C. to about −4° C.

In another aspect, the present invention provides a fresh *Ophiocordyceps sinensis* product prepared by the method described herein, wherein a water content of the humidified one or more fresh *Ophiocordyceps sinensis* is from about 4% to about 6% more than that before treating with atomized water when packaged.

In some embodiments, the fresh *Ophiocordyceps sinensis* product prepared by the method described herein, wherein the water content of the humidified one or more fresh *Ophiocordyceps sinensis* is about 5% more than that before treating with atomized water when packaged.

In some embodiments, the fresh *Ophiocordyceps sinensis* product comprises a tube and the one or more fresh *Ophiocordyceps sinensis* sealed therein, wherein a volume fraction of gas in the tube is oxygen from about 3% to about 7%; nitrogen from about 75% to about 92%; and carbon dioxide from about 5% to about 18%, the humidity level in the tube is about 65% to about 75%, and the water content of the one or more fresh *Ophiocordyceps sinensis* is from about 4% to about 6% more than that before treating with atomized water when packaged. Preferably, the volume fraction of gas in the tube is about 5% of oxygen, about 85% of nitrogen and about 10% of carbon dioxide. Preferably, when packaging, the water content of the humidified one or more fresh *Ophiocordyceps sinensis* is about 5% more than that before being treated with atomized water.

In some embodiments, the tube is an acrylic tube or a glass tube.

In some embodiments, the fresh *Ophiocordyceps sinensis* contains no less than 2% of cordycepic acid and no less than 0.5% of polysaccharide.

In some embodiments, the fresh *Ophiocordyceps sinensis* product comprises one, two or three of the fresh *Ophiocordyceps sinensis* provided herein.

In another aspect, the present invention provides a fresh *Ophiocordyceps sinensis* product comprising one or more fresh *Ophiocordyceps sinensis*, wherein a water content of the one or more fresh *Ophiocordyceps sinensis* increases from about 4% to about 6% through humidifying with atomized water.

In some embodiments, wherein a content of cordycepic acid of the one or more fresh *Ophiocordyceps sinensis* is not less than 2% by weight, a content of polysaccharide is not less than 0.5% by weight.

In some embodiments, the fresh *Ophiocordyceps sinensis* product further comprising a tube, the one or more fresh *Ophiocordyceps sinensis* is sealed in the tube, wherein a volume fraction of gas in the tube is oxygen from about 3% to about 7%; nitrogen from about 75% to about 92%; and carbon dioxide from about 5% to about 18%, the humidity level in the tube is about 65% to about 75%.

Definitions

The term "treat with atomized water" described herein refers to naturally absorbing moisture in an environment of water mist, which can be achieved by multiple methods such as, but not limited to, generating water mist through an ultrasonic humidifier.

The term "packaging in modified-atmosphere" described herein refers to packaging by using a container charged with a specified ratio of gas.

The symbol "%" used herein refers to the volume percentage of gas, such as about 3% to about 7% of oxygen, about 75% to about 92% of nitrogen and about 5% to about 18% of carbon dioxide; and the mass percentage for component, such as the fresh *Ophiocordyceps sinensis* contains no less than 2% of cordycepic acid and no less than 0.5% of polysaccharide.

The term "tube" used herein is not only a tube in the conventional sense, and is not limited by shape, size or material, as long as the fresh *Ophiocordyceps sinensis* contained therein would not be damaged, and the container can seal a certain amount of gas and maintain a certain level of humidity, which belongs to the tube described herein. Preferably, the tube is, but not limited to, an acrylic tube or a glass tube.

The term "storing at a low temperature" described herein, the low temperature refers to a temperature at which the *Ophiocordyceps sinensis* cells do not frostbite. In some embodiments, the temperature is "from about −20° C. to about 0° C."; in some embodiments, the temperature is "from about −15° C. to 0° C."; in some embodiments, the temperature is "from about −10° C. to about 0° C."; in some embodiments, the temperature is "from about −10° C. to about −2° C."; in some embodiments, the temperature is "from about −8° C. to about −4° C.".

The term "humidity" described herein refers to relative humidity.

The following abbreviations are used throughout the specification:
min minute, minutes
h hour, hours
° C. degree centigrade
W Watt
oxygen
$N_2$ nitrogen
$CO_2$ carbon dioxide The beneficial effects of the present invention comprise the followings:

1. The *Ophiocordyceps sinensis* is placed in an atomized water environment to moisturize in the humidifying step of the method of preparing the fresh *Ophiocordyceps sinensis* product provided herein, rather than soaked in water, which preserves nutrients or active ingredients, and makes the water content of *Ophiocordyceps sinensis* increase about 5% throughout this process. The increase in water content in the *Ophiocordyceps sinensis* provides a foundation for humidity balance in subsequent preservation thereof.

2. The *Ophiocordyceps sinensis* is packaged at a lower temperature of from about 5° C. to about 10° C. in a mixture gas of about 3% to about 7% oxygen, about 75% to about 92% nitrogen and about 5% to about 18% carbon dioxide, which effectively decreases the intensity of cell respiration, the *Ophiocordyceps sinensis* maintains a lower respiration status and the storage time of which can be prolonged significantly.

3. Furthermore, the method comprising stripping off mud covered on the one or more fresh *Ophiocordyceps sinensis* at a low temperature, brushing the one or more fresh *Ophiocordyceps sinensis* with flowing germfree physiological saline at a low temperature and cleaning ultrasonically the one or more fresh *Ophiocordyceps sinensis* for a short time with precooled germfree physiological saline within 1 hour after brushing the one or more fresh *Ophiocordyceps sinensis*, which can effectively prevent the one or more fresh *Ophiocordyceps sinensis* from turning brownish and maintain the its original golden yellow color. The one or more fresh *Ophiocordyceps sinensis* provided herein is brushed with flowing germfree physiological saline at a low temperature and then cleaned ultrasonically and has obvious germicidal effect. There is no addition of any chemical drug and no damage, which not only ensures the safety of food, but also keeps the one or more fresh *Ophiocordyceps sinensis* fresh, clean and full of nutritious, and more acceptable to people.

4. A large number of experiments conducted for the present invention shows that viability of fresh *Ophiocordyceps sinensis* cells can be well protected by sealing fresh *Ophiocordyceps sinensis* in a tube having a certain humidity after treating with atomized water and storing at a low temperature, especially at about −8° C. to about −4° C. The freshness and mouthfeel of the fresh *Ophiocordyceps sinensis* are retained, frost damage can be avoid, and the preservation of freshness period can last up to about 30 days or above, and preferably up to about 60 days or above.

5. The treatment of the product is performed at a low temperature at all times, not only to maintain the unique flavor of the fresh *Ophiocordyceps sinensis* for consumption, but also to maximize the retention of nutritious thereof, wherein the content of cordyceptic acid is ≥2%, and the content of polysaccharide is ≥0.5%.

DETAILED DESCRIPTION OF THE EMBODIMENTS

In order to make the objectives, technical solutions and advantages of the present invention more comprehsible, the present invention will be further described in details with reference to embodiments. It should be understood that the embodiments described herein are merely used to explain the present invention, and are not intended to limit it.

Quality measure method: the contents of cordyceptic acid and polysaccharide of the fresh *Ophiocordyceps sinensis* product were detected and analyzed by high performance liquid chromatography.

Freshness and activity measure method: triphenyl tetrazolium chloride (TTC) method is used for detection and analysis; this method is used to evaluate the vitality of fresh products, which is a widely used method in the detection field of fresh fungi and plants product, dehydrogenase action in cell respiration is the main mechanism, 2,3,5-triphenyl tetrazolium chloride (TTC) is reduced to red triphenylformazan (TTF) by dehydrogenase action, and a colormetric quantitative analysis is carried out. Dehydrogenase activity value representing activity of fresh *Ophiocordyceps sinensis* product can be obtained by the analysis. The larger the value, the higher the activity of the product is.

Freshness and activity of fresh *Ophiocordyceps sinensis* are closely related to the smell, color, hardness, cross section color, structure and mouthfeel thereof, etc., the fresh *Ophiocordyceps sinensis* has mild scent of mushroom smell, golden yellow surface color, plump and firm appearance, milky white/snowy white cross section color, compact cross section structure with no appearance of water production, crispy mouthfeel, refreshing and chewy, sweet and an obvious and lasting delicate fragrance. The content of nutritious and active ingredients of fresh *Ophiocordyceps sinensis* can be evaluated by its freshness.

The freshness of fresh *Ophiocordyceps sinensis* can be evaluated by dehydrogenase activity value, and also can be evaluated by smell, color, hardness, cross section color and structure. The specific standard of judgment is shown in table 1 below:

TABLE 1

Sensory evaluation table of fresh *Ophiocordyceps sinensis*

| Sensory items | Fresh *Ophiocordyceps sinensi* with different freshness | | | |
|---|---|---|---|---|
| | Very fresh | Fresh | Stale | Very stale |
| Smell | Mild scent of mushroom | Tasteless or strong scent of mushroom | A slight non-irritating peculiar smell | Obvious peculiar smell |
| Surface color | Golden yellow | Yellow | Brownish yellow | Blackish yellow or other abnormal color |
| Hardness | Plump and firm | Relatively soft | Soft and tough | Very soft |
| Section color | Milky white/ snowy white | white | Grayish white/ yellowish white | Dark white/ yellow or abnormal color |
| Cross section structure | Compact | Relatively looser than compact | Relatively loose | Very loose |
| Water production from section | Slight water production | Adequate water production | Apparent water production or dry | Severe water production |
| Mouthfeel | Crisp, refreshing and chewy | Slightly soft and tough | Moist or powdery | soft, non-chewy |
| Taste | sweet and an obvious and lasting delicate fragrance | Sweet and slightly delicate fragrance but not lasting | No delicate fragrance or a slight sense of non-irritating peculiar smell | Obvious peculiar smell |

Preservative effects of fresh *Ophiocordyceps sinensis* is evaluated through the following embodiments based on the above senses.

Example 1

Treatments of stripping off mud for 20 freshly harvested fresh *Ophiocordyceps sinensis* are performed immediately under a condition of about 6° C. Silt, eggs, *Phytophthora infestans*, etc. are lightly brushed off with a soft brush from the surface of fresh *Ophiocordyceps sinensis* and especially from the wrinkles. The fresh *Ophiocordyceps sinensis* is brushed with flowing germfree physiological saline precooled to about 6° C. for about 1 min after stripping off mud; the *Ophiocordyceps sinensis* is ultrasonically cleaned in germfree physiological saline precooled to about 4° C. for about 2 min within 1 hour after brushing with flowing water, the ultrasonic power is about 400 W; the fresh *Ophiocordyceps sinensis* is taken out and ultrasonically cleaned again with about 4° C. germfree physiological saline for about 0.5 min based on the same ultrasonic power; and then the *Ophiocordyceps sinensis* is treated with atomized water for about 20 min at about 10° C. in an ultrasonic humidifier, the relative humidity is controlled to about 65%, and the *Ophiocordyceps sinensis* is packaged in a tube charged with about 3% oxygen, about 92% nitrogen and about 5% carbon dioxide, the tube is a glass tube having airproof material, each tube has one fresh *Ophiocordyceps sinensis* which is sealed; the tube with the fresh *Ophiocordyceps sinensis* is stored at a low temperature of about −4° C.

After storing for 60 days, the following detection is carried out:

1. Appearance: The worm body of the *Ophiocordyceps sinensis* is plump and firm, the surface color is golden yellow, the cross section is compact and snowy white with no appearance of water production, there is no visible impurity such as soil and worm egg, and no mildew and decay, and the smell is slightly fishy.

2. Mouthfeel: the fresh *Ophiocordyceps sinensis* has a mild scent of mushroom smell, crispy, refreshing and chewing, sweet with an obvious and lasting delicate fragrance.

3. Content: the content of cordyceptic acid is about 2.1%, the content of polysaccharide is about 0.6%.

Example 2

Treatments of stripping off mud for 30 freshly harvested fresh *Ophiocordyceps sinensis* are performed immediately under a condition of about 10° C. Silt, eggs, *Phytophthora infestans*, etc. are lightly brushed off with a soft brush from the surface of fresh *Ophiocordyceps sinensis* and especially from the wrinkles. The fresh *Ophiocordyceps sinensis* is brushed with flowing germfree physiological saline precooled to about 3° C. for about 2 min after stripping off mud; the *Ophiocordyceps sinensis* is ultrasonically cleaned in germfree physiological saline precooled to about 4° C. for about 1.5 min within 1 h after brushing with flowing water, the ultrasonic power is about 300 W; the fresh *Ophiocordyceps sinensis* is taken out and ultrasonically cleaned again with about 4° C. germfree physiological saline for about 1 min based on the same ultrasonic power; and then the *Ophiocordyceps sinensis* is treated with atomized water for about 15 min at about 8° C. in an ultrasonic humidifier, the relative humidity is controlled to about 70%, and the *Ophiocordyceps sinensis* is packaged in a tube charged with about 7% oxygen, about 75% nitrogen and about 18% carbon dioxide, the tube is an acrylic tube having airproof material, each tube has three fresh *Ophiocordyceps sinensis* which is sealed; the tube with the fresh *Ophiocordyceps sinensis* is stored at a low temperature of about −8° C.

After storing for 60 days, the following detection is carried out:

1. Appearance: The worm body of the *Ophiocordyceps sinensis* is plump and firm, the surface color is golden yellow, the cross section is compact and snowy white with no appearance of water production, there is no visible impurity such as soil and eggs, and no mildew and decay, and the smell is slightly fishy.

2. Mouthfeel: the fresh *Ophiocordyceps sinensis* has a mild scent of mushroom smell, crispy, refreshing and chewing, sweet with an obvious and lasting delicate fragrance.

3. Content: the content of cordyceptic acid is about 2.2%, the content of polysaccharide is about 0.5%.

Example 3

Treatments of stripping off mud for 40 freshly harvested fresh *Ophiocordyceps sinensis* are performed immediately under a condition of about 8° C. Silt, eggs, *Phytophthora infestans*, etc. are lightly brushed off with a soft brush from the surface of fresh *Ophiocordyceps sinensis* and especially from the wrinkles. The fresh *Ophiocordyceps sinensis* is brushed with flowing germfree physiological saline precooled to about 4° C. for about 1 min after stripping off mud; the *Ophiocordyceps sinensis* is ultrasonically cleaned in germfree physiological saline precooled to about 4° C. for about 1.5 min within 1 hour after brushing with flowing water, the ultrasonic power is about 500 W; the fresh *Ophiocordyceps sinensis* is taken out and ultrasonically cleaned again with about 4° C. germfree physiological saline for about 1 min based on the same ultrasonic power; and then the *Ophiocordyceps sinensis* is treated with atomized water for about 18 min at about 8° C. in an ultrasonic humidifier, the relative humidity is controlled to about 75%, and the *Ophiocordyceps sinensis* is packaged in a tube charged with about 5% oxygen, about 75% nitrogen and about 10% carbon dioxide, the tube is an acrylic tube having airproof material, each tube has three fresh *Ophiocordyceps sinensis* which is sealed; the tube with the fresh *Ophiocordyceps sinensis* is stored at a low temperature of about −6° C.

After storing for 60 days, the following detection is carried out on a sample of 20 out of the 40 *Ophiocordyceps sinensis*:

1. Appearance: The worm body of the *Ophiocordyceps sinensis* is plump and firm, the surface color is golden yellow, the cross section is compact and snowy white with no appearance of water production, there is no visible impurity such as soil and eggs, and no mildew and decay, and the smell is slightly fishy.

2. Mouthfeel: the fresh *Ophiocordyceps sinensis* has a mild scent of mushroom smell, crispy, refreshing and chewing, sweet with an obvious and lasting delicate fragrance.

3. Content: the content of cordyceptic acid is about 2.2%, the content of polysaccharide is about 0.8%.

The remaining 20 out of the 40 fresh *Ophiocordyceps sinensis* are continued to be stored for 75 days, and the following detection is carried out:

1. Appearance: The worm body of the *Ophiocordyceps sinensis* is plump and slightly soft, the surface color is yellow, the cross section is compact and snowy white to white with no appearance of water production, there is no visible impurity such as soil and eggs, and no mildew and decay, and the smell is slightly fishy.

2. Mouthfeel: the fresh *Ophiocordyceps sinensis* has a mild scent of mushroom smell, crispy, refreshing, sweet with an obvious delicate fragrance.

3. Content: the content of cordyceptic acid is about 2.0%, the content of polysaccharide is about 0.5%.

Comparative Example 1: The Effect of Cleaning at Different Time after Stripping Off Mud on Color of Fresh *Ophiocordyceps sinensis*

Treatments of stripping off mud for 50 freshly harvested fresh *Ophiocordyceps sinensis* are performed immediately under a condition of about 5° C. Silt, eggs, *Phytophthora infestans*, etc. are lightly brushed off with a soft brush from the surface of fresh *Ophiocordyceps sinensis* and especially from the wrinkles. The fresh *Ophiocordyceps sinensis* are divided into groups after stripping off mud, 10 per each group, and which are brushed with flowing germfree physiological saline precooled to about 4° C. for about 1 min, and the groups are ultrasonically cleaned respectively at about 0.5 h, about 1 h, about 4 h and about 8 h after brushing with flowing water, the color changes are compared among each group. The results are shown in table 2.

TABLE 2 the effect of cleaning at different time after stripping
off mud on color of fresh *Ophiocordyceps sinensis*

| | Evaluation index | | | | |
|---|---|---|---|---|---|
| | 0.5 h | 1 h | 4 h | 8 h | 16 h |
| Color | Golden yellow | Golden yellow | Yellow | Brownish yellow | Brownish yellow |

The above indicates that cleaning at different time after tripping off mud has a great effect on color of fresh *Ophiocordyceps sinensis*, and cleaning of fresh *Ophiocordyceps sinensis* within 1 h after tripping off mud has a better color protection effect, the fresh *Ophiocordyceps sinensis* should be avoided exposing in air for too long and thereby causing browning.

Comparative Example 2: The Effect of Different Cleaning Methods on Fresh *Ophiocordyceps sinensis*

Treatments of stripping off mud for 40 freshly harvested fresh *Ophiocordyceps sinensis* are performed immediately under a condition of about 5° C. Silt, eggs, *Phytophthora infestans*, etc. are lightly brushed off with a soft brush from the surface of fresh *Ophiocordyceps sinensis* and especially from the wrinkles. The fresh *Ophiocordyceps sinensis* is brushed with flowing germfree physiological saline precooled to about 4° C. for about 1 min after stripping off mud; wherein 20 out of the 40 *Ophiocordyceps sinensis* are ultrasonically cleaned in germfree physiological saline precooled to about 4° C. for about 1.5 min within 1 hour after brushing with flowing water, the ultrasonic power is about 500 W; the fresh *Ophiocordyceps sinensis* is taken out and ultrasonically cleaned again with about 4° C. germfree physiological saline for about 1 min based on the same ultrasonic power. Wherein the remaining 20 *Ophiocordyceps sinensis* are ultrasonically cleaned in sterile water precooled to about 4° C. for about 1.5 min within 1 hour after brushing with flowing water, the ultrasonic power is about 500 W; the fresh *Ophiocordyceps sinensis* is taken out and ultrasonically cleaned again with about 4° C. sterile water for about 1 min based on the same ultrasonic power, the color of which is evaluated. The results are shown in table 3.

TABLE 3

The results based on different cleaning solution

| Different cleaning solutions | Color |
|---|---|
| Normal saline | Golden yellow |
| Sterile water | Yellow |

The above results indicate that germfree physiological saline used in ultrasonic cleaning has a better effect than sterile water, the safety of food hygiene is improved and the function of color preservation is also improved, the results indicate that ultrasonic cleaning using about 4° C. germfree physiological saline is better than using sterile water.

Comparative Example 3: The Effect of Storage in Tubes Having Different Relative Humidity on Fresh *Ophiocordyceps sinensis*

Treatments of stripping off mud for freshly harvested fresh *Ophiocordyceps sinensis* are performed immediately under a condition of about 5° C. Silt, eggs, *Phytophthora infestans*, etc. are lightly brushed off with a soft brush from the surface of fresh *Ophiocordyceps sinensis* and especially from the wrinkles. The fresh *Ophiocordyceps sinensis* is brushed with flowing germfree physiological saline precooled to about 4° C. for about 1 min after stripping off mud; *Ophiocordyceps sinensis* are ultrasonically cleaned in germfree physiological saline precooled to about 4° C. for about 1.5 min within 1 h after brushing with flowing water, the ultrasonic power is about 500 W; the fresh *Ophiocordyceps sinensis* is taken out and ultrasonically cleaned again with about 4° C. germfree physiological saline for about 1 min based on the same ultrasonic power.

160 fresh *Ophiocordyceps sinensis* treated by the above treatment are divided into 8 groups A, B, C, D, E, F, G, H randomly, 20 per each group, wherein group A is dehumidified by natural air drying, groups B, C, D, E, F, G, H are treated with atomized water in an ultrasonic humidifier for 0 min, about 5 min, about 10 min, about 15 min, about 20 min, about 40 min and about 60 min respectively. The fresh *Ophiocordyceps sinensis* are then respectively sealed in a tube charged with about 5% oxygen, about 85% nitrogen and about 10% carbon dioxide at about 5° C. to about 10° C., the tube is made of glass and sealed with sealing material, the relative humidity in the tube is about 70%; the above eight groups of fresh *Ophiocordyceps sinensis* products are + stored at about −8° C.

After 30 and 60 days respectively, 10 fresh *Ophiocordyceps sinensis* products are taken from each group respectively to evaluate the color, hardness, cross section of worm body and mouthfeel, and the cell activity of fresh *Ophiocordyceps sinensis* is characterized by the dehydrogenase activity value. The results are shown in table 4.

TABLE 4

Results of storage in tubes with different relative humidity

| Group | Evaluation index | 30th day | 60th day |
|---|---|---|---|
| A | Color | Dark yellow | Dark yellow |
| | Hardness | Soft and tough | Soft and tough |
| | Cross section of worm body | Yellow white, relatively loose, obviously dry cross section | Yellow white, relatively loose, obviously dry cross section |
| | Mouthfeel | Powdery, no delicate fragrance | Powdery, no delicate fragrance |
| | Dehydrogenase activity value (μg/g) | 0.38 | 0.30 |
| B | Color | Yellow | Dark yellow |
| | Hardness | Slightly Soft and tough | Soft and tough |
| | Cross section of worm body | Yellow white, relatively loose, relatively dry cross section | Yellow white, relatively loose, obviously dry cross section |
| | Mouthfeel | Powdery, relatively poor delicate fragrance | Powdery, relatively worse delicate fragrance |
| | Dehydrogenase activity value (μg/g) | 0.42 | 0.35 |
| C | Color | Yellow | Yellow |
| | Hardness | Slightly Soft and tough | Soft and tough |
| | Cross section of worm body | Yellow white, relatively loose, relatively dry cross section | Yellow white, relatively loose, obviously dry cross section |

TABLE 4-continued

Results of storage in tubes with different relative humidity

| Group | Evaluation index | 30th day | 60th day |
|---|---|---|---|
| | Mouthfeel | Slightly powdery, slightly poor delicate fragrance | Slightly powdery, poor delicate fragrance |
| | Dehydrogenase activity value (µg/g) | 0.46 | 0.39 |
| D | Color | Golden yellow | Yellow |
| | Hardness | Relatively firm | Slightly soft |
| | Cross section of worm body | White, slightly weak, moistened cross section | White, slightly weak, relatively dry cross section |
| | Mouthfeel | Slightly Soft and tough, slightly weak delicate fragrance | Slightly Soft and tough, slightly weak delicate fragrance which is not long lasting |
| | Dehydrogenase activity value (µg/g) | 0.51 | 0.47 |
| E | Color | Golden yellow | Golden yellow |
| | Hardness | Plump and firm | Plump and firm |
| | Cross section of worm body | milky white, compact, moistened cross section | milky white, compact, moistened cross section |
| | Mouthfeel | Crisp, refreshing, chewy, fresh fragrant | Crisp, refreshing, chewy, fresh fragrant |
| | Dehydrogenase activity value (µg/g) | 0.56 | 0.53 |
| F | Color | Golden yellow | Golden yellow |
| | Hardness | Plump and firm | Plump and firm |
| | Cross section of worm body | milky white, compact, moistened cross section | milky white, compact, moistened cross section |
| | Mouth feel | Crisp, refreshing, chewy, fresh fragrant | Crisp, refreshing, chewy, fresh fragrant |
| | Dehydrogenase activity value (µg/g) | 0.57 | 0.52 |
| G | Color | Golden yellow | Yellow |
| | Hardness | Slightly soft | Slightly soft |
| | Cross section of worm body | White, slightly weak, slight water production from cross section | White, slightly weak, slightly less water production from cross section |
| | Mouthfeel | Slightly Soft and tough, slightly weak delicate fragrance | Slightly Soft and tough, slightly weak delicate fragrance which is not long lasting |
| | Dehydrogenase activity value (µg/g) | 0.51 | 0.45 |
| H | Color | Slightly dark yellow | Dark yellow |
| | Hardness | Slightly Soft and tough | Soft and tough |
| | Cross section of worm body | Yellow white, relatively loose, relatively dry cross section | Yellow white, relatively loose, obviously dry cross section |
| | Mouthfeel | Moistening, relatively poor delicate fragrance | Moistening, relatively worse delicate fragrance |
| | Dehydrogenase activity value (µg/g) | 0.44 | 0.40 |

It can be seen from the above results that different treating time with atomized water has different effect on the storage of fresh *Ophiocordyceps sinensis* in a tube. The fresh *Ophiocordyceps sinensis* treated with atomized water in an ultrasonic humidifier for about 10 min to about 40 min after cleaning has good preservation effect within 30 days, and those treated with atomized water for about 15 min to about 20 min has the best preservation effect in particular, with the strongest cell vitality. However, for the fresh *Ophiocordyceps sinensis* which are treated with atomized water for less than about 5 min or more than about 60 min, and dehumidified by natural air drying, have an unsatisfactory preservation effect. The color and lustre is poor, prone to browning, the worm body is softened, the mouthfeel is poor, and there is seepage of liquid, which leads to the loss of nutrients. Therefore, it is observed that the fresh *Ophiocordyceps sinensis* which is treated with atomized water for about 10 min to about 40 min in an ultrasonic humidifier, and packaging in a sealed tube under certain humidity conditions is beneficial to the preservation of fresh *Ophiocordyceps sinensis*.

Comparative Example 4: The Effect of Different Storage Temperature on Fresh *Ophiocordyceps sinensis*

Treatments of stripping off mud for 360 freshly harvested fresh *Ophiocordyceps sinensis* are performed immediately under a condition of about 5° C. Silt, eggs, *Phytophthora infestans*, etc. are lightly brushed off with a soft brush from the surface of fresh *Ophiocordyceps sinensis* and especially from the wrinkles. The fresh *Ophiocordyceps sinensis* is brushed with flowing germfree physiological saline precooled to about 4° C. for about 1 min after stripping off mud; the fresh *Ophiocordyceps sinensis* is ultrasonically cleaned in germfree physiological saline precooled to about 4° C. for about 1.5 min within 1 h after brushing with flowing water, the ultrasonic power is about 500 W; the fresh *Ophiocordyceps sinensis* is taken out and ultrasonically cleaned again with about 4° C. germfree physiological saline for about 1 min based on the same ultrasonic power; and then the fresh *Ophiocordyceps sinensis* is treated with atomized water for about 18 min at about 5° C. in an ultrasonic humidifier, the relatively humidity is controlled to about 70%, and the *Ophiocordyceps sinensis* is packaged in a tube charged with about 5% oxygen, about 85% nitrogen and about 10% carbon dioxide, the tube is an acrylic tube having airproof material, each tube has one fresh *Ophiocordyceps sinensis* and is sealed; the abovementioned 360 treated fresh *Ophiocordyceps sinensis* products are divided into 6 groups, 60 each group, the groups are stored at about −40° C., about −20° C., about −8° C., about −4° C., about 0° C. and about 4° C. respectively. 10 fresh *Ophiocordyceps sinensis* products per each group are taken out every 15 days, and the color, hardness, cross section of worm body and mouthfeel of which are evaluated, the cell activity of fresh *Ophiocordyceps sinensis* is characterized by dehydrogenase activity value. The results are shown in table 5.

TABLE 5

Results of storage at different temperature

| | Evaluation index | 0th day | 15th day | 30th day | 45th day | 60th day | 75th day |
|---|---|---|---|---|---|---|---|
| −40° C. | Color | Golden yellow | Dark yellow | Brownish yellow | / | / | / |
| | Hardness | Firm | Relatively soft | Very soft | / | / | / |
| | Cross section of worm body | milky white, compact, moistened cross section or no water production | Yellow white, relatively loose, obvious water production | Yellow, loose, severe water production | / | / | / |
| | Mouth feel | Crisp, refreshing, chewy, fresh fragrant | Soft, less delicate fragrance | Soft, no delicate fragrance | / | / | / |
| | Dehydrogenase activity value (μg/g) | 0.64 | 0.35 | 0.28 | / | / | / |
| −20° C. | Color | Golden yellow | Yellow | Dark yellow | Brownish yellow | / | / |
| | Hardness | Firm | Relatively soft | Relatively soft | Very soft | / | / |
| | Cross section of worm body | milky white, compact, moistened cross section or no water production | White, mild water production from cross section | Yellow white, relatively loose, obvious water production | Yellow, loose, severe water production from cross section | / | / |
| | Mouth feel | Crisp, refreshing, chewy, fresh fragrant | Slightly soft and tough | Soft, less delicate fragrance | Soft, no delicate fragrance | / | / |
| | Dehydrogenase activity value (μg/g) | 0.63 | 0.43 | 0.35 | 0.28 | / | / |
| −8° C. | Color | Golden yellow | Golden yellow | Golden yellow | Golden yellow | Golden yellow | Yellow |
| | Hardness | Firm | Firm | Firm | Firm | Firm | realtively soft |
| | Cross section of worm body | milky white, compact, moistened cross section or no water production | milky white, compact, moistened cross section or no water production | milky white, compact, moistened cross section | milky white, compact, moistened cross section | milky white, compact, moistened cross section | White slightly weak, mild water production from cross section |
| | Mouth feel | Crisp, refreshing, chewy, fresh fragrant | Crisp, refreshing, chewy, fresh fragrant | Crisp, refreshing, chewy, fresh fragrant | Crisp, refreshing, chewy, fresh fragrant | Crisp, refreshing, chewy, fresh fragrant | Slightly soft and tough |
| | Dehydrogenase activity value (μg/g) | 0.64 | 0.58 | 0.55 | 0.51 | 0.50 | 0.48 |
| −4° C. | Color | Golden yellow | Golden yellow | Golden yellow | Golden yellow | Golden yellow | Yellow |
| | Hardness | Hard | Hard | Hard | Hard | Hard | Relatively soft |
| | Cross section of worm body | milky white, compact, moistened cross section or no water production | milky white, compact, moistened cross section or no water production | milky white, compact, moistened cross section | milky white, compact, moistened cross section | milky white, compact, moistened cross section | White, slightly weak, mild water production from cross section |

TABLE 5-continued

Results of storage at different temperature

| | Evaluation index | 0th day | 15th day | 30th day | 45th day | 60th day | 75th day |
|---|---|---|---|---|---|---|---|
| | Mouth feel | Crisp, refreshing, chewy, fresh fragrant | Crisp, refreshing, chewy, fresh fragrant | Crisp, refreshing, chewy, fresh fragrant | Crisp, refreshing, chewy, fresh fragrant | Crisp, refreshing, chewy, fresh fragrant | Slightly soft and tough |
| | Dehydrogenase activity value (μg/g) | 0.65 | 0.61 | 0.59 | 0.52 | 0.49 | 0.40 |
| 0° C. | Color | Golden yellow | Yellow | Brownish yellow | / | / | / |
| | Hardness | Firm | Relatively soft | Very soft | / | / | / |
| | Cross section of worm body | milky white, compact, moistened cross section or no water production | Yellow, obvious water production | Yellow, severe water production, molding | / | / | / |
| | Mouth feel | Crisp, refreshing, chewy, fresh fragrant | Slightly soft and tough | / | / | / | / |
| | Dehydrogenase activity value (μg/g) | 0.66 | 0.38 | 0.28 | / | / | / |
| 4° C. | Color | Golden yellow | Brownish yellow | / | / | / | / |
| | Hardness | Firm | Very soft | / | / | / | / |
| | Cross section of worm body | milky white, compact, moistened cross section or no water production | Very loose, obvious water production, molding | / | / | / | / |
| | Mouth feel | Crisp, refreshing, chewy, fresh fragrant | / | / | / | / | / |
| | Dehydrogenase activity value (μg/g) | 0.64 | 0.26 | / | / | / | / |

The above data indicate that the fresh *Ophiocordyceps sinensis* products disclosed herein stored at different temperature have different preservation effects, in which those being stored at about −8° C. to about −4° C. have a better preservation effect, with the longest preservation time. For those fresh *Ophiocordyceps sinensis* products which are stored at about −40° C., about −20° C., about 0° C. and about 4° C. for a certain time, browning occurs easily, the body of the worm is softened, the mouthfeel is poor, and there are seepage of fluid, which leads to the loss of nutrients. The reason is that the viable cell of *Ophiocordyceps sinensis* are frostbited at an ultralow temperature (about −40° C. and about −20° C.), and the critical point of icing up fresh *Ophiocordyceps sinensis* is not reached at about 0° C. or about 4° C., which is also not good for preservation.

Reference throughout this specification to "an embodiment", "some embodiments", "one embodiment", "another example", "an example", "a specific examples", or "some examples," means that a particular feature, structure, material, or characteristic described in connection with the embodiment or example is included in at least one embodiment or example of the present disclosure. Thus, the appearances of the phrases such as "in some embodiments," "in one embodiment", "in an embodiment", "in another example, "in an example", "in a specific examples", or "in some examples", in various places throughout this specification are not necessarily referring to the same embodiment or example of the present disclosure. Furthermore, the particular features, structures, materials, or characteristics may be combined in any suitable manner in one or more embodiments or examples.

Although explanatory embodiments have been shown and described, it would be appreciated by those skilled in the art that the above embodiments cannot be construed to limit the present disclosure, and changes, alternatives, and modifications can be made in the embodiments without departing from spirit, principles and scope of the present disclosure.

What is claimed is:

1. A method of preparing a fresh *Ophiocordyceps sinensis* product comprising the following steps:
   1) stripping off mud covered on one or more fresh *Ophiocordyceps sinensis* at a temperature from about 3° C. to about 15° C.;

2) brushing the one or more fresh *Ophiocordyceps sinensis* with flowing water at a temperature from about 3° C. to about 15° C.;
3) cleaning ultrasonically the one or more fresh *Ophiocordyceps sinensis* with water at a temperature from about 3° C. to about 15° C.;
4) humidifying the cleaned one or more fresh *Ophiocordyceps sinensis* with atomized water at a temperature from about 3° C. to about 15° C. for about 10 minutes to about 40 minutes;
5) packaging the humidified one or more fresh *Ophiocordyceps sinensis* by sealing the one or more humidified fresh *Ophiocordyceps sinensis* in a tube charged with a modifying atmosphere comprising oxygen from about 3% to about 7%; nitrogen from about 75% to about 92%; and carbon dioxide from about 5% to about 18% at a temperature from about 3° C. to about 15° C.; and
6) storing the tube at a temperature from about 20° C. to about 0° C. or from about 8° C. to about −4° C.

2. The method of claim 1, wherein the humidifying step 4) is carried out for about 15 minutes to about 20 minutes.

3. The method of claim 1, wherein the humidifying step 4) is carried out in an ultrasonic humidifier.

4. The method of claim 1, wherein both the flowing water used in the brushing step 2) and the water used in the cleaning step 3) are germfree physiological saline.

5. The method of claim 1, wherein the cleaning step 3) is performed within 1 hour after the brushing step.

6. The method of claim 1, wherein the modified-atmosphere in step 5) comprises about 5% of oxygen, about 85% of nitrogen and about 10% of carbon dioxide by volume fraction, based on the total amount of oxygen, nitrogen and carbon dioxide.

7. The method of claim 1, wherein in the packaging step 5) the humidity in the tube is controlled in a range from about 65% to about 75%.

8. The method of claim 6, wherein in the packaging step 5) the humidity in the tube is controlled in a range from about 65% to about 75%.

9. The method of claim 1, wherein the stripping step 1) refers to stripping off mud covered on the one or more fresh *Ophiocordyceps sinensis* at a temperature from about 5° C. to about 10° C.; wherein the brushing step 2) refers to brushing the one or more fresh *Ophiocordyceps sinensis* by using a brush with flowing germfree physiological saline precooled to a temperature from about 3° C. to about 6° C. for about 1 minute to about 2 minutes after the stripping step; wherein the cleaning step 3) refers to cleaning ultrasonically the one or more fresh *Ophiocordyceps sinensis* in germfree physiological saline precooled to a temperature from about 3° C. to 6° C. for about 1 minute to about 2 minutes within 1 hour after the brushing step; and wherein the ultrasonic power is from about 300 W to about 500 W.

10. The method of claim 1, wherein the cleaning step 3) further comprises cleaning ultrasonically a second time for about 0.5 minutes to about 1 minute with another germfree physiological saline precooled to a temperature from about 3° C. to 6° C., the ultrasonic power is from about 300 W to about 500 W.

11. The method of claim 1, wherein the stripping off mud refers to removing mud, eggs, and *Phytophthora infestans* from surface and wrinkles of the one or more fresh *Ophiocordyceps sinensis* by using a wool brush.

12. The method of claim 1, wherein the temperature in step 6) is from about −8° C. to about −4° C.

* * * * *